United States Patent [19]

Kirsch

[11] Patent Number: Plant 5,963

[45] Date of Patent: Apr. 28, 1987

[54] LILY PLANT NAMED DARLING

[75] Inventor: Ted T. Kirsch, Myrtle Point, Oreg.

[73] Assignee: Melridge Inc., Gresham, Oreg.

[21] Appl. No.: 771,578

[22] Filed: Aug. 30, 1985

[51] Int. Cl.[4] ..... A01H 5/00
[52] U.S. Cl. ..... Plt./68
[58] Field of Search ..... Plt./68

*Primary Examiner*—Robert E. Bagwill

*Attorney, Agent, or Firm*—Charles W. Rummler; John B. Lungmus

[57] ABSTRACT

A new and distinct clonal lily cultivar of the Oriental hybrid type, particularly suited for pot culture and distinguished by its short stature, its relatively large, bowl-shaped flowers of rich magenta-rose coloration, the deep rose-pink bud coloration before the flower opens, its deep green and horizontal leaves, and its long persistence both as a forced pot plant and as a field or garden grown plant.

2 Drawing Figures

BACKGROUND OF THE INVENTION

This new variety of lily plant originated as a seedling of unknown parentage discovered by me at my nursery in Arcata, Calif., in June of 1976. The large and richly colored flowers of this plant in combination with its short stature and silhouette appropriate for a pot plant cultivar prompted me to propagate this clone for further evaluation. This plant has been asexually propagated by me and under my direction at Arcata, Calif., through many successive generations produced by bulb scale propagation, natural propagation from bulblets and division, and by tissue culture originating from bulb scales. Such propagation has demonstrated that the clone retains its short habit, broad leaves, large flower size, and good bud color when forced into flower out-of-season. The successive generations of this cultivar have shown that its novel and distinctive characteristics are fixed and hold true from generation to generation.

Bulbs which have been dug at the proper stage of maturity and properly precooled can be forced into flower out-of-season with a reliable performance and without excessive bud abortion, even during periods of relatively low light, thereby showing that this clone is a valuable addition to the commercial production of potted lilies.

DESCRIPTION OF THE DRAWING

This new variety of lily plant is illustrated in the accompanying photographic drawing, which shows the upper half portion of a flowering stem of a potted plant in the upper view and a full face view of a flower of this plant together with foliage and buds in the principal view, the color rendition being as nearly true as can be reasonably obtained by conventional photographic procedures.

DESCRIPTION OF THE NEW VARIETY

The following is a detailed description of my new Oriental hybrid lily cultivar according to observations made on greenhouse grown plants at Sandy, Oreg., in the Spring of 1985, with color designations according to the R.H.S. Colour Chart published by The Royal Horticultural Society of London, England, and with nomenclature according to The International Lily Register, also published by The Royal Horticultural Society.

THE PLANT

Origin: Seedling.

Parentage: Unknown.

Classification:

*Botanic.*—Hybrid lily cultivar; Division VI-B of the Horticultural Classification of Lilies by The Royal Horticultural Society.

*Commercial.*—Oriental hybrid lily.

Form: Single stem from each bulb, erect and bushy.

Height: About 30 to 50 cm.

Growth: Compact, sturdy and vigorous, with good strength.

Foliage:

*Quantity.*—Abundant.

*Size of leaf.*—Ranging from about 5 to 10 cm. in length and about 2 cm. wide, the longest leaf being at the top of the stem.

*Shape of leaf.*—Broad lanceolate.

*Aspect.*—Leathery and glossy.

*Color.*—Upper and under sides, dark green. Chlorophyll pigmentation overlaid with anthocyanin.

Bulbs:

*Size.*—Varying with age; ranging up to about 30 cm. in circumference.

*Color.*—White, with flushes of soft pink or yellow which deepen as the bulbs become larger or are exposed to light.

THE BUD

Form: Generally oblong-ovate with obtuse base and acute apex.

Size: About 10 to 12 cm. in length and about 5 cm. in circumference, depending upon light and nutritional levels.

Opening rate: The bud opens slowly, in response to morning light; buds open successively from the lowermost to the uppermost, typical of Lilium.

Color: Medium magenta-rose, RHS Red-Purple 63 C-D, just before buds open, shading to softer tones at the bud tips.

Peduncle: About 2 to 3 cm. long and of dark green color. The peduncle may elongate under low light conditions or when bulbs have been improperly stored prior to forcing.

THE FLOWER

Blooming habit: Flowering annually in mid-season and profusely. Flowers occur in late July under field conditions in Arcata, Calif.; and when properly forced from appropriately precooled bulbs, the plant will flower in 95 to 110 days in the greenhouse.

Size of flower: Large, averaging 20 to 22 cm. in diameter, recurving to about 15 to 18 cm. wide. The recurving of the tepals forms a "bowl" 4 to 4.5 cm. deep.

Borne: As a compact raceme with each pedicel bearing one bud. Bulbs of typical commercial size bear an average of 5 to 8 flowers.

Shape: Bowl-shaped with broad and overlapping tepals, slightly recurved.

Tepalage:

*Number.*—Six.

*Shape.*—Generally ovoid with the uppermost tepals averaging about 5 cm. wide and the lower tepals about 3 cm. wide.

*Arrangement.*—Normal.

*Color.*—The basic color is Red-Purple, RHS 62 C-D, with a deeper band of RHS 63B 1 cm. wide along the tepal midrib, shading laterally through 62 C-D to 63C along the outer 2 cm. at the tepal margins, the inner or lower tepal margins being lightly frilled. Papillae are RHS 63B; and the nectaries are green, with a 3 to 4 mm. wide yellow margin.

*Color change.*—The color fades slightly and becomes more brown as the flower ages or in intense light and heat. Under cool conditions, the color is richer and retained longer.

*Tepal longetivity.*—Tepals stay on the stem about 2 to 3 weeks.

Pedicel:

*Length.*—About 7 to 8 cm. ascending at about 45° from the stem axis.

*Color.*—Dark green.

Fragrance: The fragrance is heavy and sweet.

Disease resistance: The flower and plant are adequately resistant to disease as observed at Arcata, Calif.

Persistence: The flowers are long lasting, both on field grown plants and as forced potted plants.

THE REPRODUCTIVE ORGANS

Stamens, anthers:

*Arrangement.*—Typical of Lilium and six in number.

*Color.*—RHS 180 A-B.

Filaments: About 7 to 8 cm. long and soft pink to white in color.

Pistils:

*Number.*—One per flower.

Style: Light green to white in color, sometimes slightly pink.

Stigma: Large and purple-grey in color.

The cumulative features of this new lily plant indicate this cultivar to have definite advantages of commercial value and in general this new plant provides a valuable addition to the commercial production of potted lilies.

I claim:

1. A new and distinct variety of Oriental hybrid lily, substantially as herein shown and described, characterized by its short stature, its short but broad leaves of dark green color, its outwardly facing, bowl-shaped flowers of very large size and of a magenta-rose coloration, and its reliable forcing performance as a pot plant cultivar.

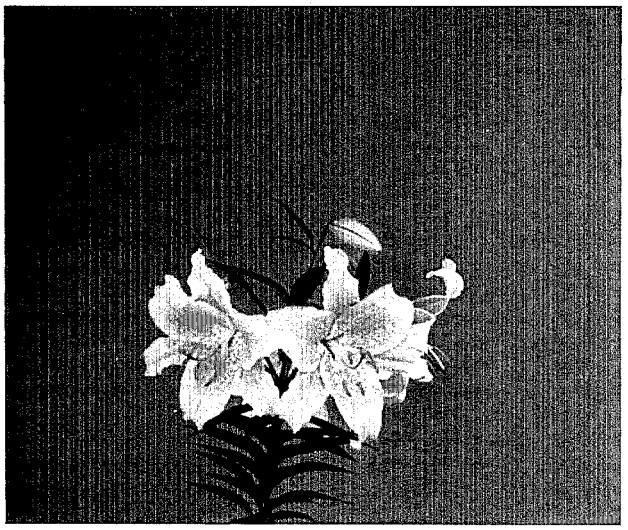
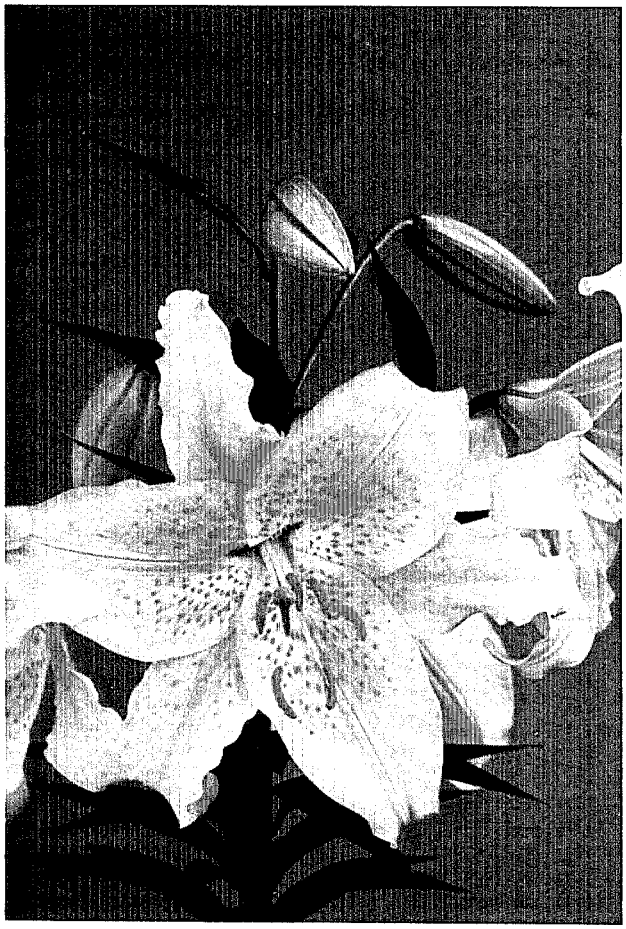

* * * * *